United States Patent [19]

Molko

[11] 4,397,312

[45] Aug. 9, 1983

[54] CLIP APPLYING FORCEPS

[75] Inventor: William P. Molko, Philadelphia, Pa.

[73] Assignee: Dittmar & Penn Corp., Phila., Pa.

[21] Appl. No.: 274,468

[22] Filed: Jun. 17, 1981

[51] Int. Cl.³ .................... A61B 17/12; A61B 17/28; A61B 17/04

[52] U.S. Cl. ................ 128/325; 128/334 R; 128/322

[58] Field of Search .................. 128/334 R, 325, 326, 128/321, 322

[56] References Cited

U.S. PATENT DOCUMENTS

| 945,292 | 1/1910 | Sether | 128/321 |
|---|---|---|---|
| 1,973,569 | 9/1934 | Kurtz | 128/321 |
| 2,631,565 | 3/1953 | Siebrandt | 128/321 |
| 2,854,005 | 9/1958 | Vido | 128/321 |

FOREIGN PATENT DOCUMENTS

| 124267 | 11/1914 | Fed. Rep. of Germany | 128/321 |
|---|---|---|---|
| 480768 | 6/1916 | France | 128/321 |
| 989926 | 9/1951 | France | 128/321 |
| 2039243 | 8/1980 | United Kingdom | 128/322 |

Primary Examiner—Kyle L. Howell
Assistant Examiner—C. W. Shedd
Attorney, Agent, or Firm—Z. T. Wobensmith, 2nd; Z. T. Wobensmith, III

[57] ABSTRACT

A forceps for applying metal clips for surgical use is disclosed, the clips being applied to blood vessels to shut off flow through the blood vessel, the forceps being capable of being opened to a much greater extent than heretofore, by shifting the position of a spring which normally opens the forceps to the extent necessary for picking up the clip to be applied.

1 Claim, 8 Drawing Figures

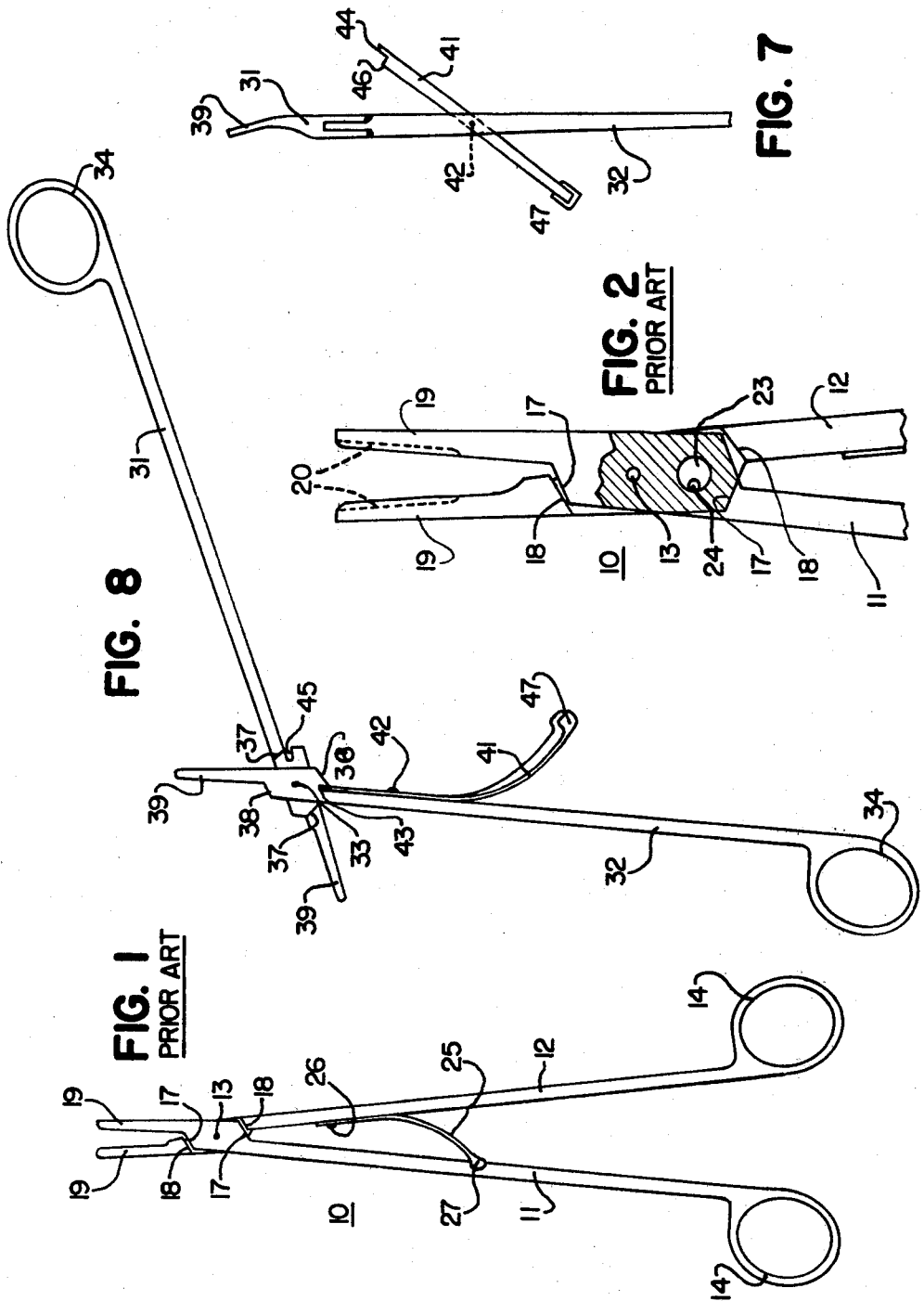

U.S. Patent  Aug. 9, 1983  Sheet 2 of 2  4,397,312
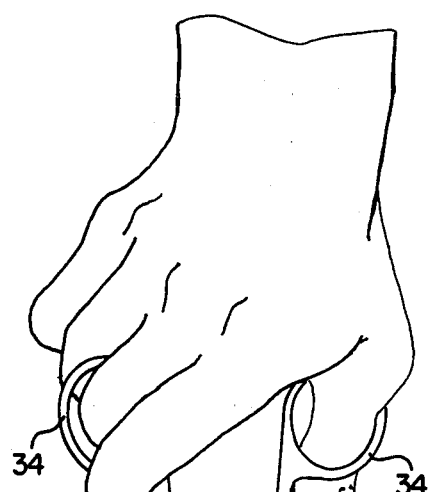
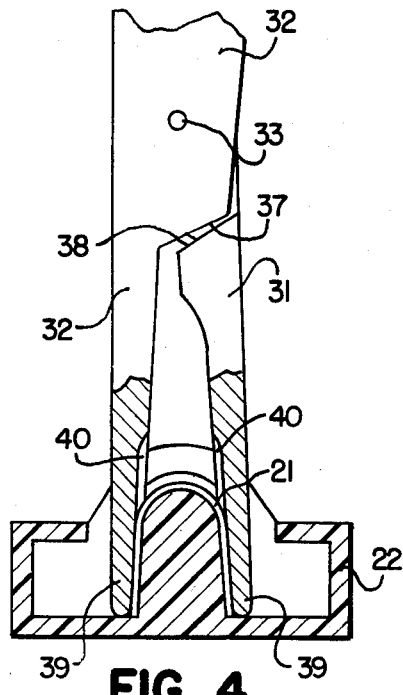
FIG. 4
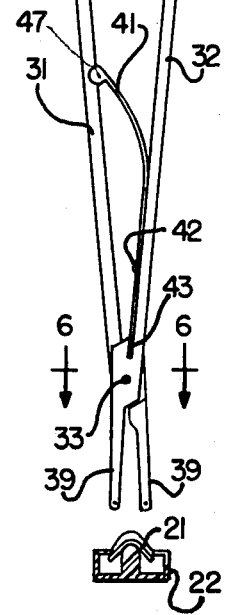
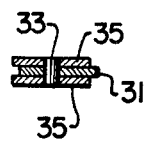
FIG. 6
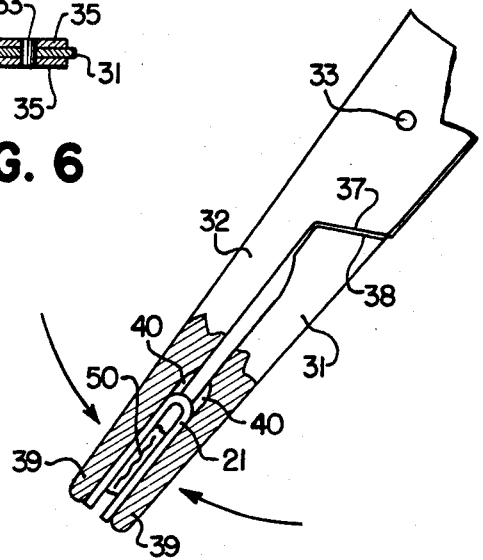
FIG. 5
FIG. 3

CLIP APPLYING FORCEPS

BACKGROUND OF THE INVENTION

1. Field of the Invention

This invention relates to forceps for applying clips to blood vessels to shut off the flow therethrough or therefrom.

2. Description of the Prior Art

It has heretofore been proposed to provide forceps as hereinafter described in detail for applying metal clips for surgical use to blood vessels to shut off flow therethrough. The structure of the forceps only permitted movement through a few degrees from a position for receiving the clip to a position for closing the slip into clamped engagement with a blood vessel. The limited pivotal action permitted with the prior forceps made removal of blood from the forceps for cleaning very difficult.

SUMMARY OF THE INVENTION

In accordance with the invention clip applying forceps are disclosed normally opened by a spring between the actuating arms of the forceps to a position to receive a clip to be applied to a blood vessel, the spring being pivotally carried on one arm and being engaged with the other arm and movable from a position permitting limited opening movement to receive a clip to a position with the legs separated at about 120° to permit proper cleaning of the forceps.

It is the principal object of the invention to provide clip applying forceps which can have the arms of the forceps opened wide for cleaning.

It is a further object of the invention to provide clip applying forceps which normally open by spring action on the arms to the desired extent for clip engagement but with which swinging of the spring to a position to permit wide opening of the arms is available.

Other objects and advantageous features of the invention will be apparent from the description and claims.

BRIEF DESCRIPTION OF THE DRAWINGS

The nature and characteristic features of the invention will be more readily understood from the following description taken in connection with the accompanying drawings forming part hereof in which:

FIG. 1 is a view in elevation as seen from one side of the prior art clip applying forceps;

FIG. 2 is a view similar to FIG. 1 but on a larger scale with parts being broken away to show the structure for limiting the separation of the arms of the forceps;

FIG. 3 is a view in elevation of the forceps in accordance with the invention and illustrating the position of the forceps prior to picking up a clip contained in a clip container;

FIG. 4 is an enlarged view in front elevation showing the picking up of a clip from the clip container, parts being broken away to show the details of construction;

FIG. 5 is a view similar to FIG. 4 but showing the clip in closed position;

FIG. 6 is an enlarged sectional view taken approximately on the line 6—6 of FIG. 3;

FIG. 7 is a view in side elevation with the spring swung to a position to permit wide separation of the arms; and FIG. 8 is a view in front elevation showing the arms in widely separated relation.

It should, of course, be understood that the description and drawings herein are illustrative merely and that various modifications and changes can be made in the structure disclosed without departing from the spirit of the invention.

Like numerals refer to like parts throughout the several views.

DESCRIPTION OF THE PRIOR ART AND OF THE PREFERRED EMBODIMENT

Referring now more particularly to FIGS. 1 and 2 of the drawings one of the prior art clip applying forceps is there illustrated. The forceps shown generally at 10 includes arms 11 and 12 pivotally connected by a pivot pin 13. In a preferred embodiment the lengths of the arms 11 and 12 will be of the order of ten and one half inches. The arms 11 and 12 can be provided with end loops 14 for insertion of the fingers for operating the forceps. One of the arms, such as the arm 11 is provided with spaced portions 15 to provide a box like structure to receive and retain an intermediate portion 16 of the arm 12, and through which the pivot pin 13 extends. The arm 12 has beveled portions 17 for engagement with complemental beveled portions 18 on the arm 11 to limit the closing movement of the arms 11 and 12.

The ends 19 of the arms 11 and 12 are both inclined in the same direction as shown in FIGS. 1 and 2 and have slots 20 for the reception of a metal wire clip 21 which clips 21 are normally stored in spaced relation in a clip receptacle 22.

In order to limit the opening of the ends 19 the intermediate portion 16 of the arm 12, as shown in FIG. 2, has a drilled hole 23 and the spaced portions 16 or the arm 11 and the hole 23 in the intermediate portion 16 or the arm 12 have a stop pin 25 extending therethrough, the stop pin 25 and hole 23 being sized to control the opening of the ends 19. The stop pin 25 is inserted in holes drilled in the box lock area of the forceps the hole in the male portions in the arm 11 being of larger diameter than the matching hole in the female portion in the arm 12. After insertion of the stop pin 24 it is surface welded on both sides of the female portion of the box lock.

A spring 25 is provided, secured to one of the arms, such as the arm 12, by a pin 26 with a U-shaped clip 27 for engagement with the other arm 11 to normally separate the ends 19 so that they may be engaged with a clip 21 positioned within the slots 20 and closed as hereinafter explained in gripping and closing engagement with a blood vessel.

With the present invention, as will hereafter be apparent the drilling of the hole 23 and the insertion of the stop pin 24 are eliminated, resulting in fewer operations with resultant ease of manufacture, reduction of the number of rejects because of improper positioning of the stop hole 23 and stop pin 25 and welding problems which have arisen, permits repair of the forceps and permits the forceps 30 to be opened widely for sterilization in a manner not heretofore possible.

Referring now to FIGS. 3 to 8, inclusive, the forceps 30 there illustrated in accordance with the present invention, includes legs 31 and 32 as before pivotally connected at their distal ends by a pivot pin 33 and of the length previously indicated. End loops 34 for insertion of the fingers of the user are provided at their proximal ends. A box lock comprising spaced portions 35 is provided on the arm 11 with the arm 12 having an intermediate portion 36 with beveled portions 37 on the arm 32 for engagement with complemental beveled portions 38 on the arm 11 to limit the opening and closing movement of the arms 31 and 32.

The ends 39 of the arms 31 and 32 are both inclined in the same direction, at an angle and have slots 40 for the reception of a metal wire clip 21 normally stored as before in a clip receptacle 22.

One of the arms and preferably the arm 32 has a leaf spring 41 pivotally secured thereto by a pivot pin 42 and swingable about the pin 42. The spring 41 has a U-shaped clip 47 for resilient engagement with the arm 32 but may be moved away from the arm 32 if it is desired to swing the spring 41 about its pivot pin 42.

In order to position the arms 31 and 32 in separated position for engagement with a clip 21, a slot 43 is provided in the arm 32 aligned with the inner edge of that arm for engagement by an end portion 44 of the spring 41 and a slot 45 is provided in the arm 31 aligned with the inner edge of that arm for engagement by an edge portion 46 of the spring 41.

When it is desired to open up the forceps 30 the clip 47 is moved out of engagement with the arm 31 and the spring 41 is turned about its pivot pin 42 to the position shown in FIG. 7 to move its distal end out of engagement with the slots 43 and 45. The arms 31 and 32 can then be moved to the open position shown in FIG. 8 thereby permitting cleaning of the forceps 30 in a manner not heretofore available and permitting repairs if necessary.

When it is desired to return the forceps 30 to a position for picking up a clip 21 the arms 31 and 32 are positioned close to their clip pick-up position, the spring 41 is moved to the position shown in FIG. 3 with the end of the spring in the groove 43 and the arm 31 is rotated clockwise so that the edge portion 46 will engage in the slot 45 when the ends 39 are in proper spaced relation for engagement with a clip 21.

In FIG. 5 the clip 21 is shown in gripping and holding relation to a blood vessel 50.

I claim:

1. Forceps for moving a clip into engagement with a blood vessel comprising
    first and second arms pivotally connected at their distal ends and having handle means at their proximal ends,
    said arms having clip deforming jaws extending from each arm distal to the pivotal connection,
    a leaf spring pivotally connected to said first arm intermediate the arms of the spring,
    the distal end of the spring being alignable with said first arm and when so aligned the proximal end is urged by the spring to bias said second arm away from said first arm,
    slots in said first and second arms proximal to the pivotal connection therebetween which are engageable with the distal end of said spring when said spring is substantially aligned with said first arm whereby said jaws are properly spaced to engage an undeformed clip therebetween,
    said slots being located such that said jaws are closeable to deform the clip when said spring is engaged in said slots.

* * * * *

UNITED STATES PATENT AND TRADEMARK OFFICE
CERTIFICATE OF CORRECTION

PATENT NO. : 4,397,312

DATED : August 9, 1983

INVENTOR(S) : WILLIAM P. MOLKO

It is certified that error appears in the above-identified patent and that said Letters Patent is hereby corrected as shown below:

Column 2,

Line 33, after "16", "or" should be -- of --

Column 4,

Claim 1, line 17, "arms" should be -- ends --

Signed and Sealed this

Fourteenth Day of February 1984

[SEAL]

Attest:

GERALD J. MOSSINGHOFF

Attesting Officer     Commissioner of Patents and Trademarks